United States Patent
Ghinovker

(10) Patent No.: US 8,138,498 B2
(45) Date of Patent: Mar. 20, 2012

(54) APPARATUS AND METHODS FOR DETERMINING OVERLAY OF STRUCTURES HAVING ROTATIONAL OR MIRROR SYMMETRY

(75) Inventor: Mark Ghinovker, Migdal Ha'Emek (IL)

(73) Assignee: KLA-Tencor Technologies Corporation, Milpitas, CA (US)

(*) Notice: Subject to any disclaimer, the term of this patent is extended or adjusted under 35 U.S.C. 154(b) by 0 days.

(21) Appl. No.: 12/410,317

(22) Filed: Mar. 24, 2009

(65) Prior Publication Data
US 2009/0224413 A1 Sep. 10, 2009

Related U.S. Application Data

(60) Division of application No. 11/227,764, filed on Sep. 14, 2005, now Pat. No. 7,541,201, which is a continuation-in-part of application No. 09/894,987, filed on Jun. 27, 2001, now Pat. No. 7,068,833, and a continuation-in-part of application No. 10/729,838, filed on Dec. 5, 2003, now Pat. No. 7,317,531.

(60) Provisional application No. 60/229,256, filed on Aug. 30, 2000, provisional application No. 60/698,535, filed on Jul. 11, 2005, provisional application No. 60/440,970, filed on Jan. 17, 2003, provisional application No. 60/449,496, filed on Feb. 22, 2003, provisional application No. 60/431,314, filed on Dec. 5, 2002, provisional application No. 60/504,093, filed on Sep. 19, 2003, provisional application No. 60/498,524, filed on Aug. 27, 2003.

(51) Int. Cl.
*H01L 23/58* (2006.01)
*H01L 29/10* (2006.01)

(52) U.S. Cl. .................. 257/48; 257/797; 257/E23.179
(58) Field of Classification Search .................. 257/48, 257/797, E23.179
See application file for complete search history.

(56) References Cited

U.S. PATENT DOCUMENTS

| | | | |
|---|---|---|---|
| 4,251,160 | A | 2/1981 | Bouwhuis et al. |
| 4,475,811 | A | 10/1984 | Brunner |
| 4,538,105 | A | 8/1985 | Ausschnitt |
| 4,703,434 | A | 10/1987 | Brunner |
| 4,714,874 | A | 12/1987 | Morris et al. |
| 4,757,207 | A | 7/1988 | Chappelow et al. |
| 4,757,707 | A | 7/1988 | Harvey et al. |

(Continued)

FOREIGN PATENT DOCUMENTS
EP 0818814 1/1998
(Continued)

OTHER PUBLICATIONS

Bishop, et al, "The OMAG3 Reticle Set," Jul. 31, 2003, International SEMATECH, Technology Transfer #3074417A-ENG, pp. 1-26.

(Continued)

*Primary Examiner* — Jarrett J Stark
(74) *Attorney, Agent, or Firm* — Weaver Austin Villeneuve & Sampson LLP

(57) ABSTRACT

Disclosed are overlay targets having flexible symmetry characteristics and metrology techniques for measuring the overlay error between two or more successive layers of such targets. Techniques for imaging targets with flexible symmetry characteristics and analyzing the acquired images to determine overlay or alignment error are disclosed.

11 Claims, 7 Drawing Sheets

U.S. PATENT DOCUMENTS

| | | | |
|---|---|---|---|
| 4,778,275 A | 10/1988 | van den Brink et al. |
| 4,782,288 A | 11/1988 | Vento |
| 4,820,055 A | 4/1989 | Müller |
| 4,855,253 A | 8/1989 | Weber |
| 4,929,083 A | 5/1990 | Brunner |
| 5,017,514 A | 5/1991 | Nishimoto |
| 5,100,237 A | 3/1992 | Wittekoek et al. |
| 5,112,129 A | 5/1992 | Davidson et al. |
| 5,148,214 A | 9/1992 | Ohta et al. |
| 5,156,982 A | 10/1992 | Nagoya |
| 5,172,190 A | 12/1992 | Kaiser |
| 5,216,257 A | 6/1993 | Brueck et al. |
| 5,262,258 A | 11/1993 | Yanagisawa |
| 5,296,917 A | 3/1994 | Kusonose et al. |
| 5,383,136 A | 1/1995 | Cresswell et al. |
| 5,414,514 A | 5/1995 | Smith et al. |
| 5,436,097 A | 7/1995 | Norishima et al. |
| 5,438,413 A | 8/1995 | Mazor et al. |
| 5,477,057 A | 12/1995 | Angeley et al. |
| 5,479,270 A | 12/1995 | Taylor |
| 5,481,362 A | 1/1996 | Van Den Brink et al. |
| 5,498,501 A | 3/1996 | Shimoda et al. |
| 5,596,413 A | 1/1997 | Stanton et al. |
| 5,617,340 A | 4/1997 | Cresswell et al. |
| 5,627,083 A | 5/1997 | Tounai et al. |
| 5,665,495 A | 9/1997 | Hwang |
| 5,674,650 A | 10/1997 | Dirksen et al. |
| 5,699,282 A | 12/1997 | Allen et al. |
| 5,701,013 A | 12/1997 | Hsia et al. |
| 5,702,567 A | 12/1997 | Mitsui et al. |
| 5,703,685 A | 12/1997 | Senda et al. |
| 5,712,707 A | 1/1998 | Ausschnitt et al. |
| 5,757,507 A | 5/1998 | Ausschnitt et al. |
| 5,766,809 A | 6/1998 | Bae |
| 5,783,342 A | 7/1998 | Yamashita et al. |
| 5,805,290 A | 9/1998 | Ausschnitt et al. |
| 5,835,196 A | 11/1998 | Jackson |
| 5,857,258 A | 1/1999 | Penzes et al. |
| 5,872,042 A | 2/1999 | Hsu et al. |
| 5,877,036 A | 3/1999 | Kawai |
| 5,877,861 A | 3/1999 | Ausschnitt et al. |
| 5,882,980 A | 3/1999 | Bae |
| 5,902,703 A | 5/1999 | Leroux et al. |
| 5,912,983 A | 6/1999 | Hiratsuka |
| 5,923,041 A | 7/1999 | Cresswell et al. |
| 5,939,226 A | 8/1999 | Tomimatu |
| 5,949,145 A | 9/1999 | Komuro |
| 5,968,693 A | 10/1999 | Adams |
| 6,020,966 A | 2/2000 | Ausschnitt et al. |
| 6,023,338 A | 2/2000 | Bareket |
| 6,037,671 A | 3/2000 | Kepler |
| 6,077,756 A | 6/2000 | Lin et al. |
| 6,079,256 A | 6/2000 | Bareket |
| 6,084,679 A | 7/2000 | Steffan et al. |
| 6,118,185 A | 9/2000 | Chen et al. |
| 6,128,089 A | 10/2000 | Ausschnitt et al. |
| 6,130,750 A | 10/2000 | Ausschnitt et al. |
| 6,137,578 A | 10/2000 | Ausschnitt |
| 6,140,217 A | 10/2000 | Jones et al. |
| 6,146,910 A | 11/2000 | Cresswell et al. |
| 6,160,622 A | 12/2000 | Dirksen et al. |
| 6,165,656 A | 12/2000 | Tomimatu |
| 6,177,330 B1 | 1/2001 | Yasuda |
| 6,278,957 B1 | 8/2001 | Yasuda et al. |
| 6,384,899 B1 | 5/2002 | den Boef |
| 6,462,818 B1 | 10/2002 | Bareket |
| 6,580,505 B1 * | 6/2003 | Bareket .................. 356/401 |
| 6,617,080 B1 | 9/2003 | Kawachi et al. |
| 6,638,671 B2 | 10/2003 | Ausschnitt et al. |
| 6,921,916 B2 | 7/2005 | Adel et al. |
| 6,937,337 B2 | 8/2005 | Ausschnitt et al. |
| 6,985,618 B2 | 1/2006 | Adel et al. |
| 6,992,764 B1 | 1/2006 | Yang et al. |
| 7,068,833 B1 | 6/2006 | Ghinovker et al. |
| 7,177,457 B2 | 2/2007 | Adel et al. |
| 7,181,057 B2 | 2/2007 | Adel et al. |
| 7,274,814 B2 | 9/2007 | Ghinovker et al. |
| 7,289,213 B2 | 10/2007 | Mieher et al. |
| 7,301,634 B2 | 11/2007 | Mieher et al. |
| 7,317,531 B2 | 1/2008 | Mieher et al. |
| 7,317,824 B2 | 1/2008 | Ghinovker et al. |
| 7,355,291 B2 | 4/2008 | Adel et al. |
| 7,473,502 B1 | 1/2009 | Ausschnitt et al. |
| 7,474,401 B2 | 1/2009 | Ausschnitt et al. |
| 7,541,201 B2 | 6/2009 | Ghinovker |
| 7,700,247 B2 | 4/2010 | Ausschnitt et al. |
| 2002/0080364 A1 | 6/2002 | Monshouwer et al. |
| 2004/0233442 A1 | 11/2004 | Mieher et al. |
| 2006/0197950 A1 | 9/2006 | Smith et al. |
| 2009/0224413 A1 | 9/2009 | Ghinovker |

FOREIGN PATENT DOCUMENTS

| | | |
|---|---|---|
| EP | 0947828 | 6/1999 |
| JP | 11-87213 | 7/1989 |
| JP | 8-116141 | 5/1996 |
| JP | 10-213896 | 8/1998 |
| JP | 11067631 | 9/1999 |
| JP | 11-307418 | 11/1999 |
| JP | 2001-093819 | 4/2001 |
| JP | 2001-267202 | 9/2001 |
| JP | 2004-508711 | 3/2004 |
| WO | 02-19415 | 3/2002 |

OTHER PUBLICATIONS

International Search Report dated Jan. 5, 2007 issued in PCT/US06/25836.

Written Opinion of the International Searching Authority dated Jan. 5, 2007 issued in PCT/US04/05419.

Hsu et al., "Characterizing lens distortion to overlay accuracy by using fine measurement pattern", Mar. 1999, SPIE vol. 3677.

Office Action of U.S. Appl. No. 09/894,987 mailed Jul. 2, 2004. (7,068,833).

Office Action of U.S. Appl. No. 09/894,987 mailed Jun. 22, 2005. (7,068,833).

Notice of Allowance of U.S. Appl. No. 09/894,987 mailed Feb. 1, 2006. (7,068,833).

Notice of Allowance dated Aug. 16, 2007 for U.S. Appl. No. 11/394,938 7,317,824.

Office Action of U.S. Appl. No. 10/184,013 mailed Aug. 25, 2004. (6,985,618).

Notice of Allowance of U.S. Appl. No. 10/184,013 mailed Aug. 31, 2005. (6,985,618).

Office Action of U.S. Appl. No. 10/184,026 mailed Aug. 25, 2004. (7,177,457).

Notice of Allowance of U.S. Appl. No. 10/184,026 mailed Jan. 4, 2006. (7,177,457).

Office Action of U.S. Appl. No. 10/186,324 mailed Aug. 25, 2004. (7,181,057).

Final Office Action of U.S. Appl. No. 10/186,324 mailed Sep. 6, 2005. (7,181,057).

Notice of Allowance of U.S. Appl. No. 10/186,324 dated Nov. 21, 2005. (7,181,057).

Levinson, "Lithography Process Control", Tutorial Texts in Optical Engineering, Mar. 1999, vol. TT28, Chapter 5, pp. 94-107.

Final Office Action of U.S. Appl. No. 10/185,737 mailed Dec. 3, 2003. (6,921,916).

Office Action of U.S. Appl. No. 10/185,737 mailed Jun. 5, 2003. (6,921,916).

Office Action of U.S. Appl. No. 10/185,737 mailed Jun. 30, 2004. (6,921,916).

Notice of Allowance of U.S. Appl. No. 10/185,737 mailed Mar. 29, 2005. (6,921,916).

Rivera et al., "Overlay Performance on Tungsten CMP Layers Using the ATHENA Alignment System", 2000, Proceeding of SPIE vol. 3998.

Office Action Mailed May 5, 2006 from U.S. Appl. No. 11/179,819 7,355,291.

Office Action Mailed Aug. 21, 2007 from U.S. Appl. No. 11/179,819 7,355,291.

Notice of Allowance Mailed Nov. 19, 2007 from U.S. Appl. No. 11/179,819 7,355,291.

Notice of Allowance dated May 18, 2007 for U.S. Appl. No. 11/432,947 7,274,814.
Office Action dated Mar. 27, 2009 for U.S. Appl. No. 11/830,782.
Final Office Action dated Dec. 14, 2009 issued in U.S. Appl. No. 11/830,782.
Office Action dated Apr. 2, 2010 for U.S. Appl. No. 11/830,782.
Final Office Action dated Oct. 6, 2010 for U.S. Appl. No. 11/830,782.
Written Opinion of the International Searching Authority dated Mar. 11, 2002 issued in PCT/US01/41932.
International Search Report dated Jan. 24, 2002 issued in PCT/US01/41932.
Office Action dated Jun. 25, 2010 for U.S. Appl. No. 12/533,295.
Final Office Action dated Oct. 7, 2010 for U.S. Appl. No. 12/533,295.
US Office Action dated Apr. 9, 2008 issued in U.S. Appl. No. 11/227,764.
Notice of Allowance dated Dec. 15, 2008 issued in 11/227,764.
Notice of Reason for Refusal, Japanese Patent Application No. 2008-521428, dated May 31, 2011.
US 5,841,144, 11/1998, Cresswell (withdrawn)

* cited by examiner

APPARATUS AND METHODS FOR DETERMINING OVERLAY OF STRUCTURES HAVING ROTATIONAL OR MIRROR SYMMETRY

CROSS REFERENCE TO RELATED PATENT APPLICATION

This application claims priority and is a Divisional application of copending application Ser. No. 11/227,764, entitled "APPARATUS AND METHODS FOR DETERMINING OVERLAY OF STRUCTURES HAVING ROTATIONAL OR MIRROR SYMMETRY", filed 14 Sep. 2005 by Mark Ghinovker, which application claims priority of (a) and is a Continuation-in-part application of application Ser. No. 09/894,987, filed on Jun. 27, 2001, now U.S. Pat. No. 7,068,833, issued on 27 Jun. 2006, which claims priority of Application No. 60/229,256, filed 30 Aug. 2000 and (b) U.S. Provisional Patent Application No. 60/698,535, entitled "APPARATUS AND METHODS FOR DETERMINING OVERLAY STRUCTURES HAVING ROTATIONAL OR MIRROR SYMMETRY", filed 11 Jul. 2005 by Mark Ghinovker, and (c) is a Continuation-in-part application of application Ser. No. 10/729,838, filed on Dec. 5, 2003, now U.S. Pat. No. 7,317,531, issued on 8 Jan. 2008, which application claims priority of (i) Application No. 60/440,970, filed 17 Jan. 2003, (ii) Application No. 60/449,496, filed 22 Feb. 2003, (iii) Application No. 60/431,314, filed 5 Dec. 2002, (iv) Application No. 60/504,093, filed 19 Sep. 2003, and (v) Application No. 60/498,524, filed 27 Aug. 2003. These applications and patents are incorporated herein by reference in their entirety for all purposes.

BACKGROUND OF THE INVENTION

The present invention relates generally to overlay measurement techniques, which are used in semiconductor manufacturing processes. More specifically, the present invention relates to techniques for measuring alignment error between different layers or different patterns on the same layer of a semiconductor wafer stack.

The measurement of overlay error between successive patterned layers on a wafer is one of the most critical process control techniques used in the manufacturing of integrated circuits and devices. Overlay accuracy generally pertains to the determination of how accurately a first patterned layer aligns with respect to a second patterned layer disposed above or below it and to the determination of how accurately a first pattern aligns with respect to a second pattern disposed on the same layer. Presently, overlay measurements are performed via test patterns that are printed together with layers of the wafer. The images of these test patterns are captured via an imaging tool and an analysis algorithm is used to calculate the relative displacement of the patterns from the captured images.

The most commonly used overlay target pattern is the "Box-in-Box" target, which includes a pair of concentric squares (or boxes) that are formed on successive layers of the wafer. The overlay error is generally determined by comparing the position of one square relative to another square.

To facilitate discussion, FIG. 1 is a top view of a typical "Box-in-Box" target 10. As shown, the target 10 includes an inner box 12 disposed within an open-centered outer box 14. The inner box 12 is printed on the top layer of the wafer while the outer box 14 is printed on the layer directly below the top layer of the wafer. As is generally well known, the overlay error between the two boxes, along the x-axis for example, is determined by calculating the locations of the edges of lines c1 and c2 of the outer box 14, and the edge locations of the lines c3 and c4 of the inner box 12, and then comparing the average separation between lines c1 and c3 with the average separation between lines c2 and c4. Half of the difference between the average separations c1&c3 and c2&c4 is the overlay error (along the x-axis). Thus, if the average spacing between lines c1 and c3 is the same as the average spacing between lines c2 and c4, the corresponding overlay error tends to be zero. Although not described, the overlay error between the two boxes along the y-axis may also be determined using the above technique.

This type of target has a same center of symmetry (COS) for both the x and y structures, as well as for the first and second layer structures. When the target structures are rotated 180° about their COS, they maintain a same appearance. Conventionally, it has been a requirement that both the x and y structures and both the first and second layer structures have a same COS. However, these requirements may be too restrictive under certain conditions. For example, space may be limited on the wafer and a target having x and y structures (or first and second layer structures) with the same COS may not fit into the available space. Additionally, it may be desirable to use device structures for determining overlay, and device structures are not likely to meet this strict requirement.

Although this conventional overlay design has worked well, there are continuing efforts to provide improved techniques for determining or predicting overlay in device structures. For example, targets or device structures that have more flexible symmetry characteristics, as well as techniques for determining overlay with such structures, are needed.

SUMMARY OF THE INVENTION

In general, overlay targets having flexible symmetry characteristics and metrology techniques for measuring the overlay error between two or more successive layers of such targets or a shift between two sets of structures on the same layer are provided. In one embodiment, a target includes structures for measuring overlay error (or a shift) in both the x and y direction, wherein the x structures have a different center of symmetry (COS) than the y structures. In another embodiment, one of the x and y structures is invariant with a 180° rotation and the other one of the x and y structures has a mirror symmetry. In one aspect, the x and y structures together are variant with a 180° rotation. In yet another example, a target for measuring overlay in the x and/or y direction includes structures on a first layer having a 180 symmetry and structures on a second layer having mirror symmetry. In another embodiment, a target for determining overlay in the x and/or y direction includes structures on a first layer and structures on a second layer, wherein the structures on the first layer have a COS that is offset by a known amount from the COS of the structures on the second layer. In a specific implementation, any of the disclosed target embodiments may take the form of device structures. In a use case, device structures that have an inherent 180° rotational symmetry or a mirror symmetry in each of the first and second layers are used to measure overlay in a first layer and a second layer. Techniques for imaging targets with flexible symmetry characteristics and analyzing the acquired images to determine overlay or alignment error are disclosed.

In one embodiment, a semiconductor target for determining a relative shift between two or more successive layers of a substrate or between two or more separately generated patterns on a single layer of a substrate is disclosed. This target includes a plurality of first structures having a first center of symmetry (COS) or first line of symmetry (LOS) and being arranged to determine the relative shift in an x direction by analyzing an image of the first structures. This target further includes a plurality of second structures having a second COS or second LOS and being arranged to determine the relative shift in an x direction by analyzing an image of the second structures. The first COS or LOS has a different location than the second COS or LOS.

In a further aspect, the first structures have a first LOS about which the first structures have a mirror symmetry or the first structures have a 180° rotational symmetry with respect to the first COS, and the second structures have a first LOS about which the second structures have a mirror symmetry or the second structures have a 180° rotational symmetry with respect to the second COS. In another aspect, the first and second structures are in the form of device structures. In a further embodiment, a one of the first or second structures has a 180° rotational symmetry with respect to its COS and the other one of the first or second structures' has a mirror symmetry with respect to its LOS. In yet a further implementation, the first structures and the second structures together are variant with a 180° rotational asymmetry or together have a mirror asymmetry.

In an alternative embodiment, a semiconductor target for determining an overlay error between two or more successive layers of a substrate is disclosed. This target comprises a plurality of first structures formed in a first semiconductor layer and having a first center of symmetry or first line of symmetry (LOS) and a plurality of second structures formed in a second semiconductor layer and having a second COS OR LOS. The first COS OR LOS is designed to have a known offset from the second COS or LOS so that the overlay error can be determined by acquiring an image of the first and second structures and then analyzing a shift between the first and second COS's or LOS's in the image and comparing the shift to the known offset.

In a specific implementation, the first structures have a first LOS about which the first structures have a mirror symmetry or the first structures have a 180° rotational symmetry with respect to the first COS, and the second structures have a first LOS about which the second structures have a mirror symmetry or the second structures have a 180° rotational symmetry with respect to the second COS. In yet a further aspect, the first and second structures are in the form of device structures. In another implantation, a one of the first or second structures has a 180° rotational symmetry with respect to its COS and the other one of the first or second structures' has a mirror symmetry with respect to its LOS. In a further implementation, the first structures and the second structures together are variant with a 180° rotational asymmetry or together have a mirror asymmetry.

In another embodiment, the invention pertains to a method for determining the relative shift between two or more successive layers of a substrate or between two or more separately generated patterns on a single layer of a substrate. A first image is acquired of a plurality of first structures having a first center of symmetry (COS) or first line of symmetry (LOS) and being arranged to determine the relative shift in an x direction by analyzing an image of the first structures. A first image is acquired of a plurality of second structures having a second COS or second LOS and being arranged to determine the relative shift in an x direction by analyzing an image of the second structures. The first COS or LOS has a different location than the second COS or LOS. The first image of the first structures' COS is analyzed to determine whether the first structures have a shift in the x direction that is out of specification, and the second image of the second structures' COS is analyzed determine whether the second structures have a shift in the y direction that is out of specification.

In a specific aspect, the first and second images are acquired together in a same field of view. In another aspect, analyzing the first image comprises (i) when it is determined that the first structures fail to have a 180 rotational or mirror symmetry, determining that the first structures are out of specification; and (ii) when it is determined that the second structures fail to have a 180 rotational or mirror symmetry, determining that the second structures are out of specification. In another feature, analyzing the first image and analyzing the second image each includes (i) using outside edges of each region of interest of the first or second image to determine a COS or LOS for a first set of substructures and a COS or LOS for a second set of substructures, and (ii) when the COS or LOS of the first set of substructures differs from the COS or LOS of the second set of substructures by more than a predetermined amount, determining that the corresponding structures are out of specification. In a further aspect, the first set of substructures are formed from a first layer and the second set of substructures are formed from a second layer.

In yet another implementation, analyzing the first image and analyzing the second image each includes (i) for a first set of substructures, selecting an initial COS or LOS between a plurality of regions of interest, (ii) for the first set of substructures, automatically placing its 180 degree or mirror counterpart based on the initial COS or LOS, respectively, for each of the first and second images, (iii), for the first set of substructures, continuing to move the initial COS or LOS until a best correlation is found between the first substructures and their counterpart, (iv) repeating operations (i) through (iii) for a second set of substructures, (v) when a best correlation is found for both the first and second substructures and when the COS or LOS of the first set of substructures differs from the COS or LOS of the second set of substructures by more than a predetermined amount, determining that the corresponding first structures are out of specification. In a further aspect, the first set of substructures are formed from a first layer and the second set of substructures are formed from a second layer.

In a further method embodiment, the overlay error between two or more successive layers of a substrate is determined. An image is acquired of a plurality of first structures formed in a first semiconductor layer and having a first center of symmetry (COS) or line of symmetry (LOS) and a plurality of second structures formed in a second semiconductor layer and having a second COS or LOS. The first COS or LOS is designed to have a known offset from the second COS or LOS so that the overlay error can be determined by acquiring an image of the first and second structures and then analyzing a shift between the first and second COS's or LOS's in the image and comparing the shift to the known offset. The image of the first and second structures' COS or LOS is analyzed to determine whether there is an overlay error between the first and second structures that is out of specification.

In a specific implementation, the first structures have a first LOS about which the first structures have a mirror symmetry or the first structures have a 180° rotational symmetry with respect to the first COS, and the second structures have a first LOS about which the second structures have a mirror symmetry or the second structures have a 180° rotational symmetry with respect to the second COS. In another implementation, the first and second structures are in the form of device structures. In another embodiment, a one of the first or second structures has a 180° rotational symmetry with respect to its COS and the other one of the first or second structures' has a mirror symmetry with respect to its LOS. In another aspect, the first structures and the second structures together are variant with a 180° rotational asymmetry or together have a mirror asymmetry.

These and other features and advantages of the present invention will be presented in more detail in the following specification of the invention and the accompanying figures which illustrate by way of example the principles of the invention.

BRIEF DESCRIPTION OF THE DRAWINGS

The present invention is illustrated by way of example, and not by way of limitation.

DETAILED DESCRIPTION OF THE INVENTION

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, the present invention provides semiconductor targets for determining an overlay error between two process layers or a shift between two sets of structures on the same layer, where the target structures are designed with a known relationship between their symmetry characteristics. Although the following target examples are shown to have structures on two layers for measuring overlay, it is readily apparent that each target may include two sets of structures on the same layer for determining a shift error between such set of structures.

Figure 1:
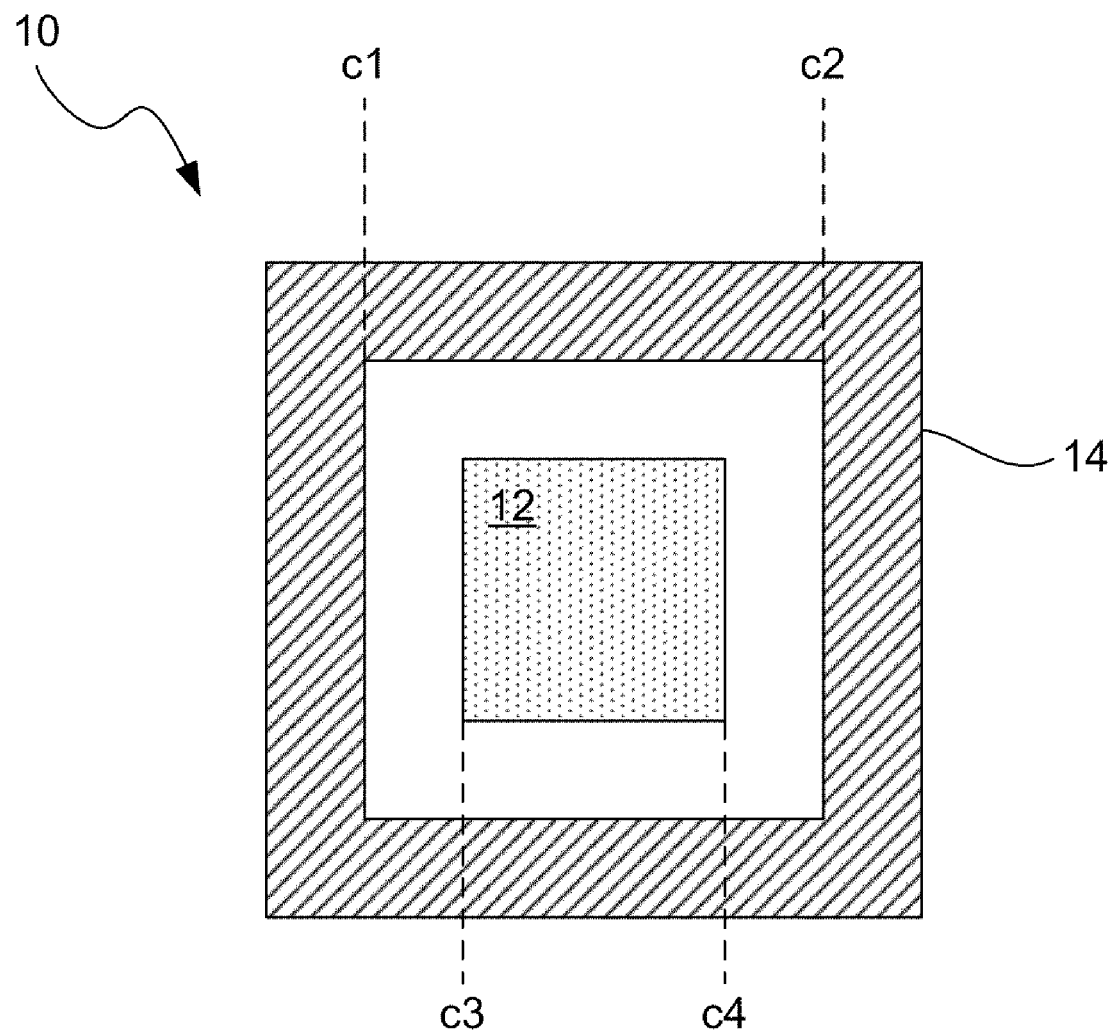
FIG. 1 is a top plan view of a box-in-box type overlay mark.
Figure 2:
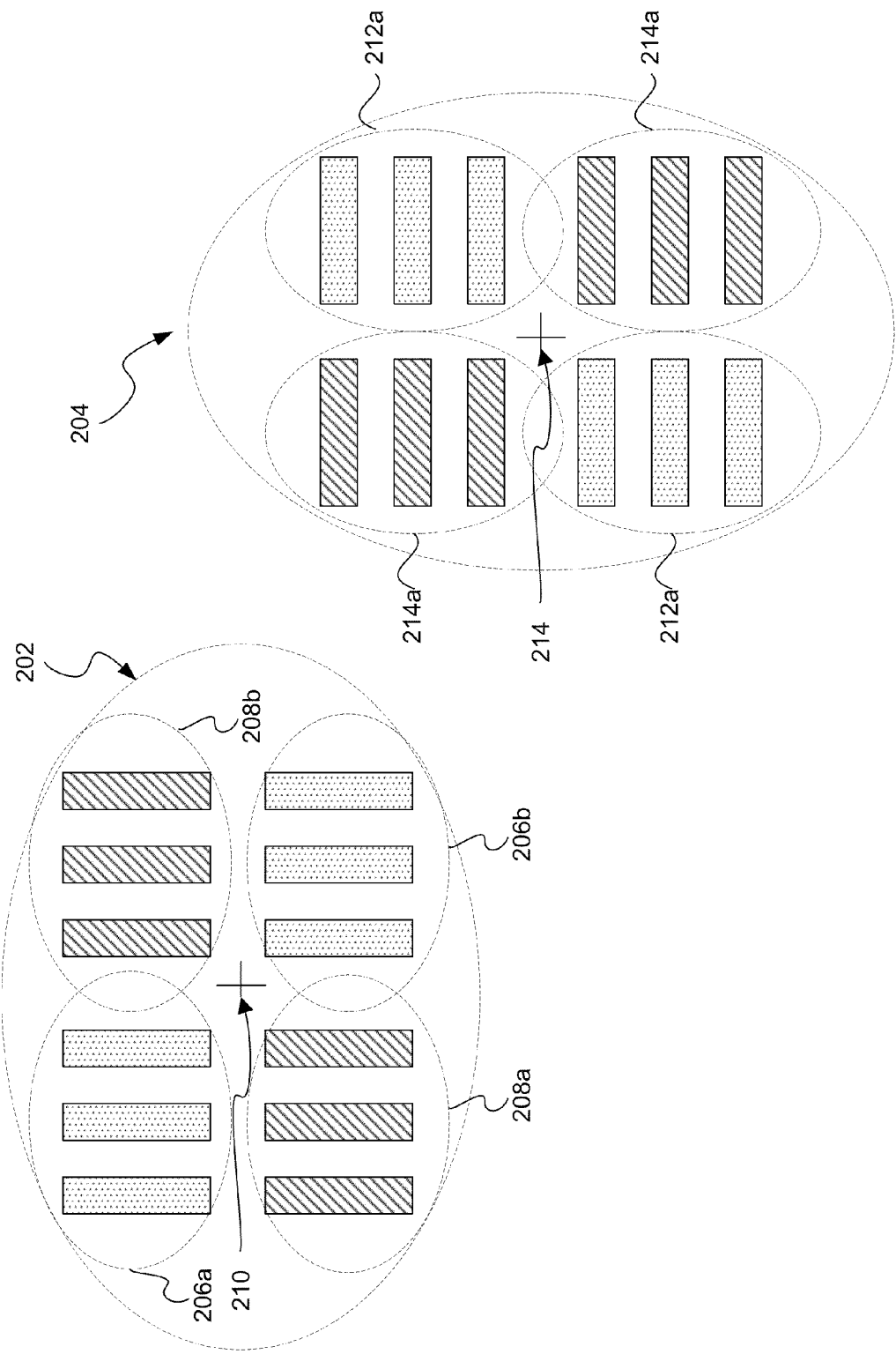
FIG. 2 is a top plan view of overlay targets for measuring overlay error between two different process layers in both an x and y direction in accordance with one embodiment of the present invention.

FIG. 2 is a top plan view of overlay targets for measuring overlay error between two different process layers in both an x and y direction in accordance with one embodiment of the present invention. As shown, a first target 202 is arranged for measuring an overlay error between a set of first structures 206 in a first layer and a set of second structures 208 in a second layer with respect to an x direction. A second target 204 is arranged for measuring an overlay error between a set of first structures 212 in a first layer and a set of second structures 214 in a second layer with respect to a y direction.

In this embodiment, each of the x and y targets are designed so that its first structures have a same 180° rotational center of symmetry as its second structures although the x direction target 202 is designed to have a center of symmetry (COS) 210 that has a different location than the y direction target 204 COS 214. For example, the x direction target 202 has first structures that are divided into two groups 206a and 206b that are positioned with respect to each other so that if they were rotated 180° about a center of symmetry 210, the first structures would have a same appearance before and after such rotation. The x direction target 204 also includes second structures 208 that are divided into two groups 208a and 208b that are positioned with respect to each other so that if they were rotated 180° about a center of symmetry 210, the first structures would have a same appearance before and after such rotation. In this illustration, the COS of the first structures is at the same position as the COS of the second structures. When a overlay error is present within a target, the COS of the first structures of such target is shifted from the COS of the second structures. This shift is called the overlay error.

The overlay error in separate x and y targets may be determined based on a priori knowledge that each target is designed to have structures in each layer that have a 180° rotational symmetry about a same COS. Any shift between the COS's of the first and second layer structures may be imaged and measured as an overlay error. In alternative embodiments, the x and/or y targets of FIG. 2 may be arranged so that the first and second structures have a COS with a known offset. In this case, if the shift does not match the known offset, the amount of variance corresponds to the overlay error.

Figure 3:
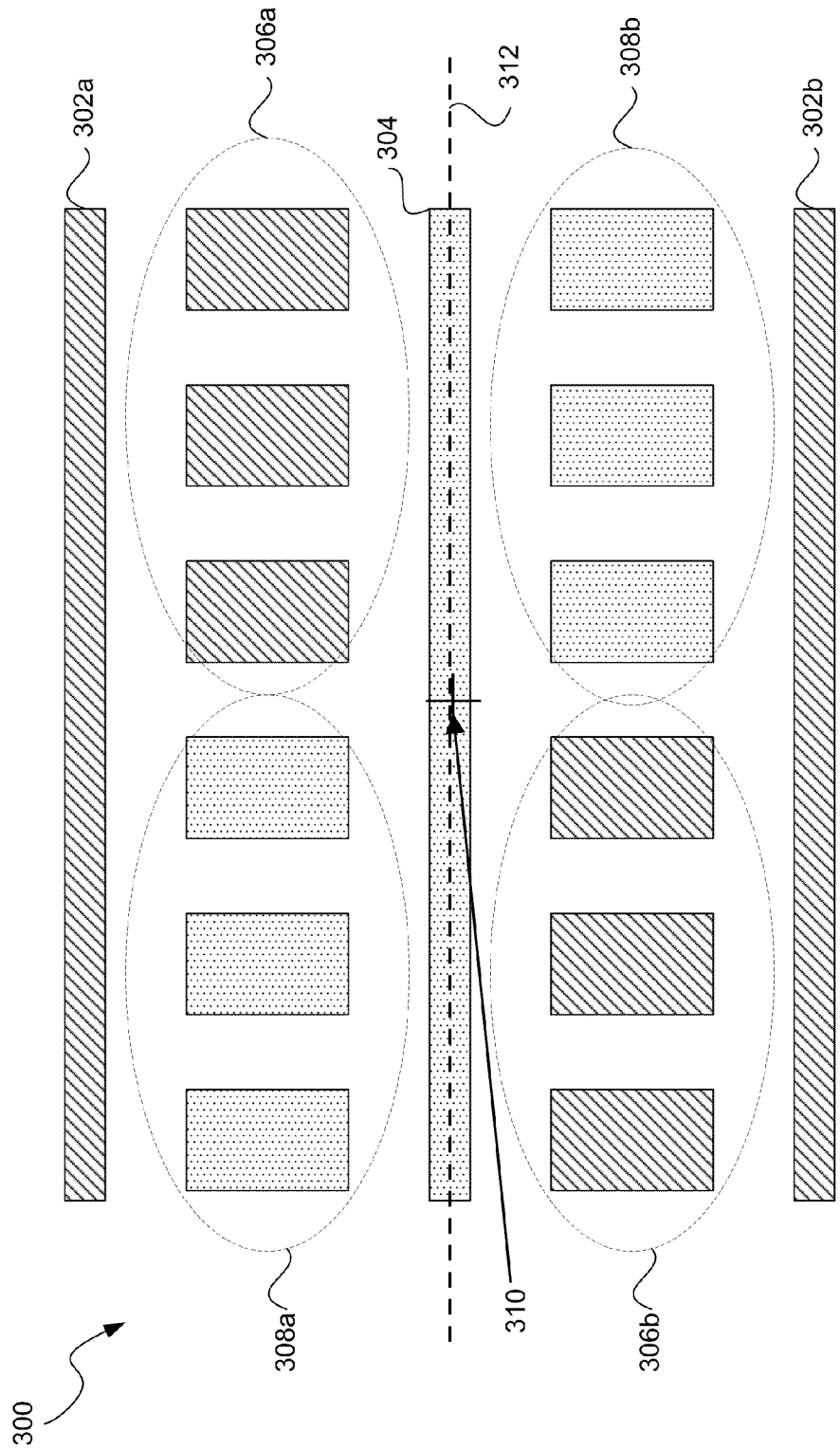
FIG. 3 is a diagrammatic top view an overlay target, wherein one of its x and y direction structures has a 180° rotational symmetry while the other of its x and y direction structures has a mirror symmetry, in accordance with an alternative embodiment of the present invention.

FIG. 3 is a diagrammatic top view an overlay target 300, wherein one of its x and y direction structures has a 180° rotational symmetry while the other of its x and y direction structures has a mirror symmetry, in accordance with an alternative embodiment of the present invention. As shown, the target 300 includes x direction structures 306 and 308 and y direction structures 302 and 304. The x direction structures include a first set of structures 306a and 306b on a first layer and a second set of structures 308a and 308b on a second layer. The y direction structures include a first set of structures 302a and 302b on a first layer and a single structure 304 on a second layer. The first and second structures of the x direction target are designed to have a 180° rotational symmetry with respect to a same center of symmetry (COS) 310, while the first and second structures of the y direction target are designed to have a mirror symmetry with respect to a same line of symmetry (LOS) 312. A shift between either the COS's or LOS's of the first and second layer structures can be imaged and measured to determine an overlay error in the x or y direction, respectively. In alternative embodiments, the x and/or y targets of FIG. 3 may be arranged so that the first and second structures have COS's or LOS's with a known offset. In this case, if the shift does not match the known offset, the amount of variance corresponds to the overlay error.

Targets having flexible symmetry characteristics may be in the form of device structures. In other words, device structures which have inherent symmetrical properties, such as a 180 rotational symmetry and/or a mirror symmetry for structures in a first and second layer may be used. These structures may also have a known offset between their COS's or LOS's. Such devices may be identified by the designer and identified by tags in the design layout. Alternatively, such "target" devices may be located manually or automatically after fabrication.

Figure 4A:
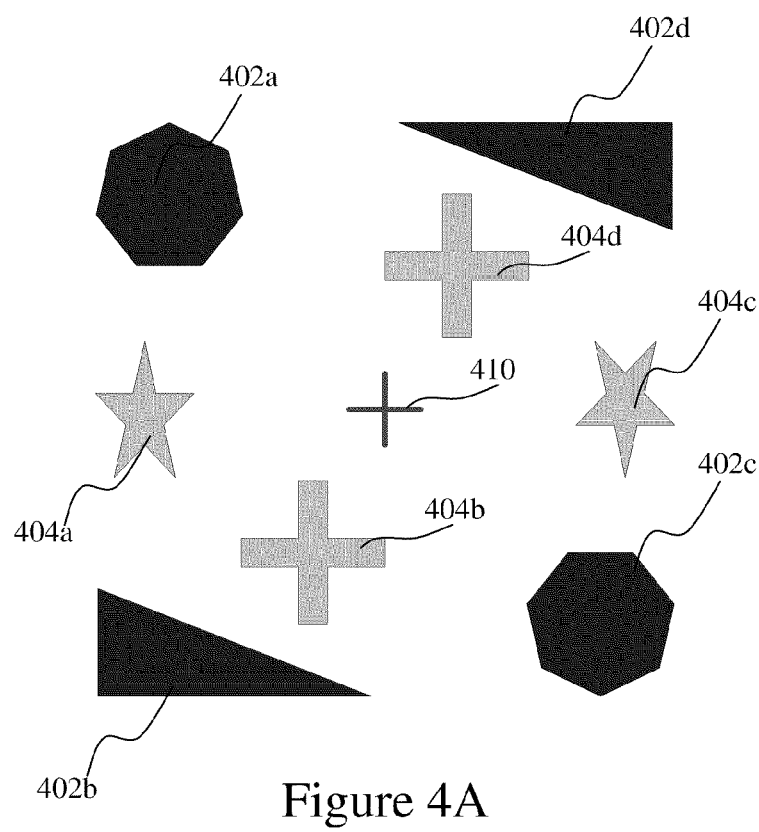
FIG. 4A is a diagrammatic top view of an overlay target in accordance with a specific implementation of the present invention.
Figure 4B:
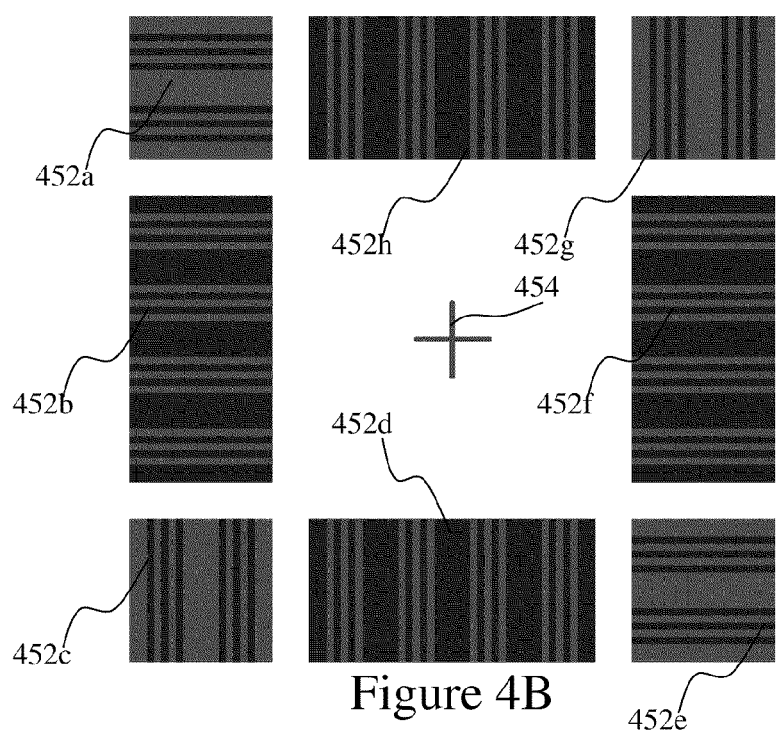
FIG. 4B is a diagrammatic top view of an overlay target in accordance with an alternative implementation of the present invention.

The target structures of the present invention may have any suitable shape and arrangement so as to provide flexible symmetry characteristics. FIGS. 4A and 4B illustrate various examples of target shapes and arrangements. Although the targets are shown as having structures on a first layer with a same COS as structures on a second layer, the first and second layer structures may easily be designed to have different COS's. These FIGS. 4A and 4B are merely meant to illustrate the different shapes that the targets of the present invention may take.

FIG. 4A is a diagrammatic top view of an overlay target in accordance with a specific implementation of the present invention. Each set of target structures in each layer may include any number and shape of structures. A first set of structures in a first layer (shaded black) includes structure 402a through 402d which have a center of symmetry 410. Structures 402a and 402c are 7 sided polygons, while structures 402b and 402d are triangles. A second set of structures in a second layer (shaded gray) includes structure 404a through 404d which have the same center of symmetry 410 as the first set of structures in the first layer. Structures 404a and 404c are star shaped polygons, while structures 404b and 404d are cross shaped polygons. In one embodiment of the present invention, the center of symmetry of the first layer structures is offset from the center of symmetry of the second layer structures by a known distance (not shown).

FIG. 4B is a diagrammatic top view of an overlay target in accordance with an alternative implementation of the present invention. In this embodiment, each structure includes a plurality of horizontal or vertical lines in two different layers. A first layer is shaded black, while a second layer is shaded gray. Each horizontal and vertical line may also be formed from a plurality of segments (not shown). As shown, horizontal structures 452a, 452b, 452e and 452f and vertical structures 452b, 452c, 452d, 452g, and 452h have a same center of symmetry 454. Additionally, the different layers of each set of vertical and horizontal structures are shown as having a same center of symmetry. In a specific implementation of the present invention, the center of symmetry of the horizontal structures is offset from the center of symmetry vertical structures by a known distance (not shown). In another specific implementation of the present invention, the center of symmetry of the first layer structures (from the horizontal and/or vertical structures) is offset from the center of symmetry of the second layer structures (from the horizontal and/or vertical structures) by a known distance (not shown).

The target rules preferably include a requirement that the target be placed in a layer which is measurable or inspectable by a particular type of tool. For example, the target may have to be on a top layer or be covered with only optically transparent layers so that the target may be inspected by an optical tool. In other applications, the target may be required to be underneath an opaque layer so that the opaque layer's conformance to the underlying target may be inspected and/or measured. Additionally, each inspection, review, or metrology tool typically has a size constraint as to the measured or inspected structure. That is, structures below a particular size cannot be seen. Therefore, the targets must be sized so that they can be measured or inspected by the relevant tool.

The targets of the present invention described herein may be placed in any suitable space on the wafer. By way of examples, the targets may be placed in the scribe line or within the dies themselves. When targets are placed in a die, the die layout may also be analyzed to determine whether particular portions or areas have a characteristic which negatively or positively affects metrology or inspection results, as compared with other areas of the die layout. For example, particular layout characteristics may result in more reliable or accurate metrology or inspection results. In one specific case, targets may be placed in areas which have characteristics that positively affect the metrology or inspection. In an example of such a feature characteristic, a chemical mechanical polishing (CMP) procedure is typically tuned to achieve superior accuracy with a particular feature density range. Thus, targets, such as overlay targets, may be placed in layout regions which are within the particular feature density range for an optimal CMP process.

The circuit designer may be aware of feature locations in the die layout which are most susceptible to error or defects. The designer may communicate the position of such features to the target placement software or layout engineer so that targets may be placed proximate to such problem features. This placement technique would likely result in a higher incidence of defect capture and more reliable resulting products.

The targets may also be placed within a dummy layer. It is common practice in semiconductor manufacturing today to include dummy structures in open areas of the circuit layout to ensure uniform pattern density. Dummy structures are generally used for optimal results in chemical mechanical polishing and other semiconductor manufacturing processes.

In order to enable targets inside the chip area, there are significant advantages in combining the functionality of the particular metrology (or inspection) target with the purpose of the dummy structures. That is, a structure which has two components that serve both purposes of a dummy structure and a metrology (or inspection) target would efficiently utilize the open spaces of the die area to increase CMP uniformity (and other dummy requirements where applicable), as well as to provide a metrology or inspection target. Additionally, a new type of metrology or inspection may be used with such combination marks. For example, a particular design pattern's fidelity may be monitored via such combination target. That is, a designer's intent regarding a particular pattern's function or structure may be verified with respect to the pattern being combined and measured or inspected in a dummy structure.

A combination target and dummy structure can be achieved in a number of different ways. In one example of a combination dummy and overlay structure, the structures can be designed on two masks such that they form interlaced periodic structures. Any suitable types of overlay structures may be altered to have flexible COS's or LOS's as described herein. Suitably modifiable overlay targets and techniques for determining overlay with same are described in the following U.S. patents and applications: (1) U.S. Pat. No. 6,462,818, issued 8 Oct. 2002, entitled "OVERLAY ALIGNMENT MARK DESIGN", by Bareket, (2) U.S. Pat. No. 6,023,338, issued 8 Feb. 2000, entitled "OVERLAY ALIGNMENT MEASUREMENT OF WAFER", by Bareket, (3) application Ser. No. 09/894,987, filed 27 Jun. 2001, entitled "OVERLAY MARKS, METHODS OF OVERLAY MARK DESIGN AND METHODS OF OVERLAY MEASUREMENTS", by Ghinovker et al., (4) U.S. Pat. No. 6,486,954, issued 26 Nov. 2002, entitled "OVERLAY ALIGNMENT MEASUREMENT MARK" by Levy et al., (5) application Ser. No.

10/367,124, filed 13 Feb. 2004, entitled OVERLAY METROLOGY AND CONTROL METHOD, by Mike Adel et al, (6) application Ser. No. 10/785,396 filed 23 Feb. 2004, entitled APPARATUS AND METHODS FOR DETECTING OVERLAY ERRORS USING SCATTEROMETRY, by Walter D. Mieher, et al., (7) application Ser. No. 10/729,838 filed 5 Dec. 2003, entitled APPARATUS AND METHODS FOR DETECTING OVERLAY ERRORS USING SCATTEROMETRY, by Walter D. Mieher, et al., and (8) application Ser. No. 10/858,836 filed 1 Jun. 2004, entitled APPARATUS AND METHODS FOR PROVIDING IN-CHIP MICROTARGETS FOR METROLOGY OR INSPECTION, by Avi Cohen et al. These patents and applications are all incorporated herein by reference in their entirety.

An overlay type combination and dummy structure includes two components one on a first layer or mask and one on a second layer or mask. Each component preferably complies with the requirements for a dummy structure of the process step associated with that layer or mask. A further example may be a case where these periodic structures are aligned such that the component on a first mask is symmetrically positioned with respect to the component on a second mask when the masks are correctly aligned. Also, the component on a first mask may be designed to fit into the open spaces within the component on a second mask and visa versa. As a further particular example, the periodic component on the two masks could be identical but offset by half a unit cell of the periodic structure along both x and y axes. Alternatively the component on a first mask may have a different structure than the component on a second mask but is still offset by half a unit cell of the component as above. Example overlay type combination targets are shown in FIG. 4C through 4E.

Each component may also contain an additional coarse segmentation which is periodic and is designed to improve the contrast and information content for the metrology tool as further described in the above referenced U.S. application Ser. No. 10/367,124 by Mike Adel et al.

Figure 4C:
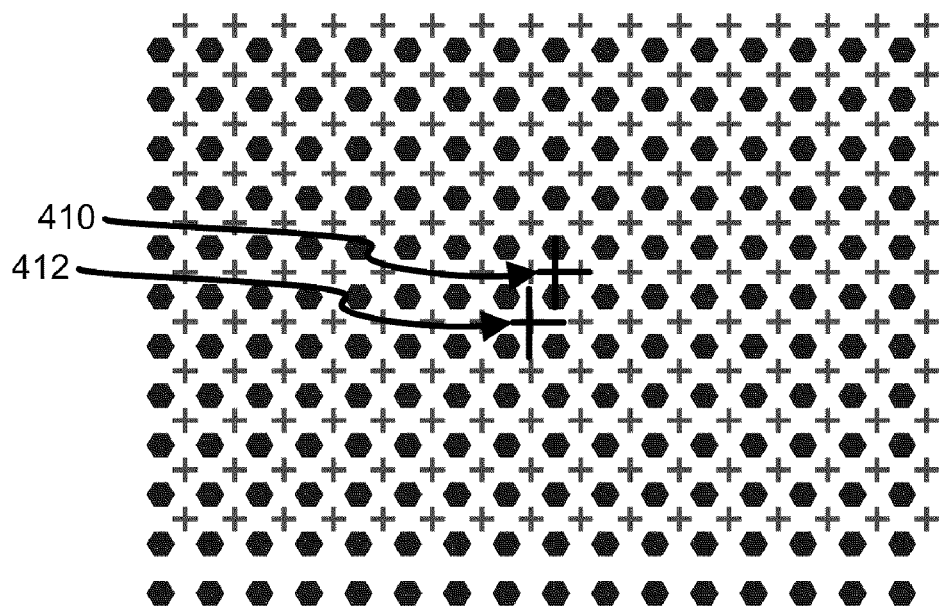
FIGS. 4C through 4E together illustrate a technique for forming combination dummy and overlay structures, as well as example structures, in accordance with specific implementations of the present invention.
Figure 4D:
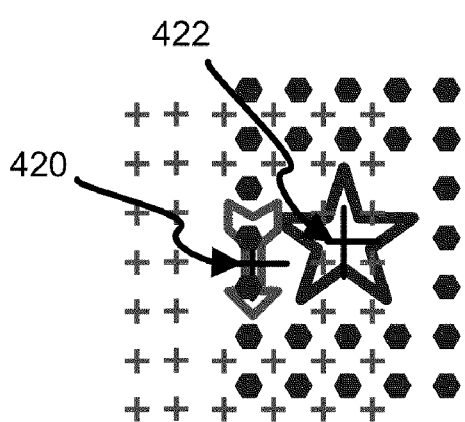
Figure 4E:
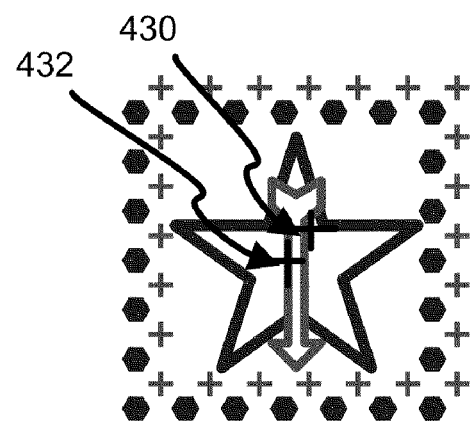

FIGS. 4C through 4E together illustrate a technique for forming combination dummy and overlay structures, as well as example structures, in accordance with specific implementations of the present invention. An open space may be filled with any suitably sized and shaped combination dummy and target structures (referred to herein as targets). As shown in FIG. 4C, an array of targets are formed within an open area. The targets include a first set of structures on a first layer (e.g., the "+" shaped structures) and a second set of structures on a second layer (e.g., the hexagon shaped structures). Note that the first set of structures has a COS 410, while the second set of structures have a second COS 412 that is offset from the first COS 410.

In another technique, an array of targets may be conceptually used to fill in around actual device structures. As shown in FIG. 4D, an array of hexagon shaped and "+" shaped structures are overlaid onto two device structures. For illustration purposes, one device structure is shaped like a star and is on a same layer as the hexagon target structures, while another device structure is shaped like an arrow and is on the same layer as the "+" shaped target structures. After the target array is overlaid with the device structures, some of the target structures are removed to accommodate the device structures. That is, target structures on one layer are removed from an area encompassing the device structure on the same layer. As shown, the "+" shaped structures are removed from an area encompassing the arrow shaped device structure, and the hexagon shaped structures are removed from an area encompassing the star shaped device structure. The target structures are removed such that a COS of each layer is maintained. For example, the first layer structures have a first COS 420 that differs from the second COS 422 of the second layer structures.

If the device structures on two different layers are overlapping, however, both layers of targets are removed from an area encompassing the two overlapping device structures as illustrated in FIG. 4E. In this example, the target structures are also removed such that a COS of each layer is maintained. For example, the first layer structures have a first COS 430 that differs from the second COS 432 of the second layer structures.

In these combination dummy and target examples, a signal is detected from the field of views (FOV's) as represented in FIGS. 4C-4E. The center of symmetries of the first and second layers are determined. In embodiments of the present invention, the center of symmetries are designed to be located at a known offset from each other so that a discrepancy can be translated into an overlay value. In alternative embodiments, a first set of structures are used to measure overlay in an x direction and a set of second structures are used to measure overlay in a y direction. The x direction structures have a center of symmetry or line of symmetry that differs from the y direction structures.

When the FOV includes both targets and devices as in FIGS. 4D and 4E, it is first determined which parts of the signal are noise (or device structures) and which parts correspond to the target structures. This determination may be determined in suitable manner. In one embodiment, the signal (or image generated from such signal) is compared to a design file which identifies device structures and the device structures' contribution to the signal (or image) is subtracted from the signal (or image). The resulting signal (or image) corresponds to the target which may then be assessed as previously described. Alternatively, one may manually train the metrology tool to locate targets by manually moving the tool to known target locations and identifying the targets. These identified targets can then be used by the metrology tool to search for other targets with a similar appearance using standard pattern recognition techniques. Alternatively, a representative target in the design file may be used to train the metrology tool. The representative target may also be located in a easily found position, such as the scribe line.

In general, rules for both dummy structures and the particular target type are followed when forming combination dummy and target structures. For instance, the dummy structure rules may require a particular pattern density or maximum open space size for ensuring a particular level of CMP uniformity. Additionally, the particular metrology or inspection procedure rules for the targets are followed. In one type of overlay metrology technique, the structures on two different layers are assessed to determine whether their centers of symmetry are where they should be (e.g., aligned or offset by a known distance) to thereby determine overlay. In this example, the structures are designed on two different layers and have a same center of symmetry or known offset centers of symmetry.

Figure 5:
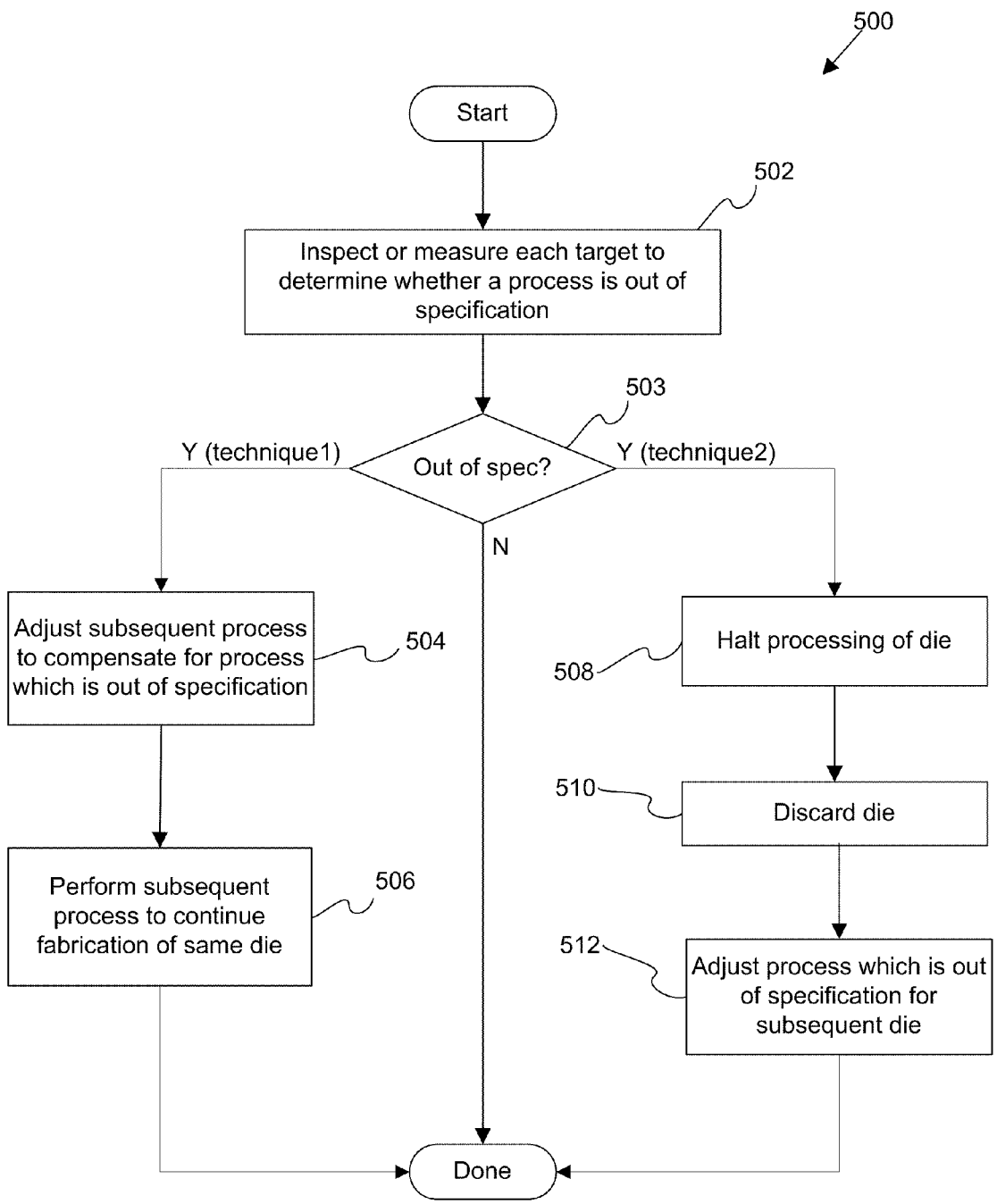
FIG. 5 is a flowchart illustrating a procedure for inspecting targets in accordance with techniques of the present invention.

After a die and targets are fabricated, the targets may be inspected, reviewed, or measured in any suitable manner. FIG. 5 is a flowchart illustrating a procedure 500 for inspecting targets fabricated from a layout pattern generated in accordance with techniques of the present invention. Initially, each target is inspected or measured to determine whether a process is out of specification in operation 502. It is then determined whether a process is out of specification in operation 503. If a process is not out of specification, the inspection, review, or measurement procedure ends.

If a process is out of specification, a number of techniques may be implemented to alleviate the problem. In a first technique, a subsequent process may be adjusted to compensate for the process which is out of specification in operation 504. For example, if it is determined that the photoresist pattern is misaligned in any portion, the photoresist may then be stripped and reapplied in a corrected pattern to eliminate the misalignment. The subsequent process is then performed so as to continue fabrication of the same die in operation 506. For example, the wafer may be patterned. In a second technique, processing of the die may be halted in operation 508. The die may then be discarded in operation 510. The process which is out of specification may then be adjusted for subsequent die(s) in operation 512.

Figure 6:
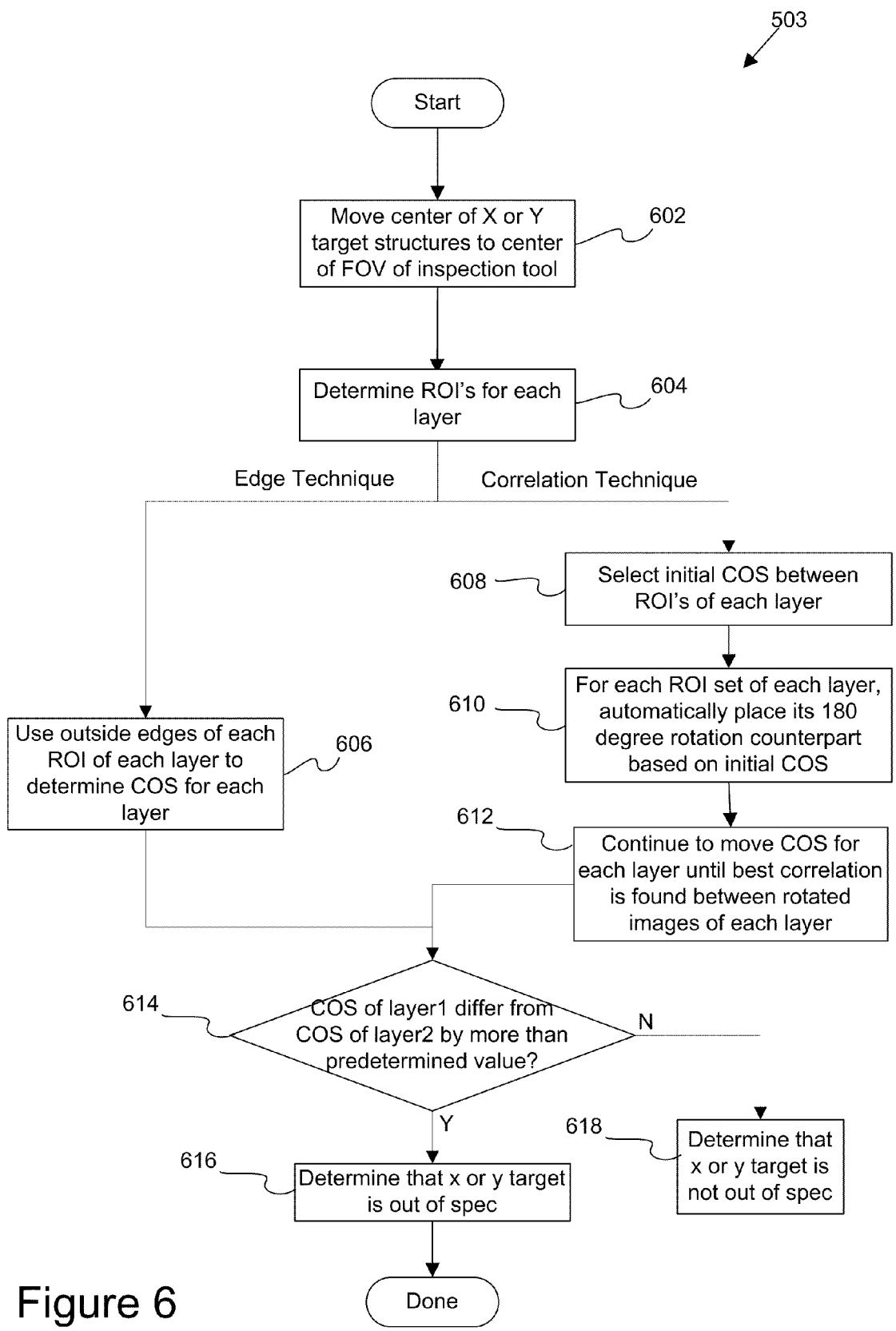
FIG. 6 is a flowchart illustrating the operation of FIG. 5 for determining whether a target is out of specification in accordance with a specific implementation of the present invention.

One may determine whether the targets with flexible COS's and/or LOS's of the present invention are within specification in any suitable manner. FIG. 6 is a flow chart illustrating the operation 503 of FIG. 5 for determining whether a target is out of specification in accordance with a specific implementation of the present invention. Although this procedure is described with respect to a target having structures with a 180° rotational COS, of course, this procedure may be easily modified for structures with mirror symmetry. This procedure may also be applied to determining an alignment error between two sets of structures on the same layer, rather than an overlay error on two different layers as illustrated.

In the illustrated example of FIG. 6, the center of either X or Y target structures are initially moved to the center of the FOV of the inspection tool in operation 602. The region of interests (ROI's) of each layer are then determined in operation 604. The x target structures of FIG. 2 will be used to illustrate the procedure of FIG. 6. For example, four ROI's may be formed for the x direction target structures 206a, 206b, 208a and 208b of FIG. 2, as represented by the dotted lines. The dotted line 202 may represent the FOV of the inspection tool, while the cross 210 represents the center of the x target structures.

The COS for each set of structures 206 and 208 from the first and second layers, respectively, may be determined using any suitable technique. For example, an edge technique may be utilized to determine COS for the structures in each layer. In the illustrated embodiment, the outside edges of each ROI of each layer are used to determine the COS for each layer in operation 606. For the structures 206 and 208, the outside edges of each ROI may be determined and then the edges are then used to find a center position between the outside edges of each set of structures (e.g., between structures 206a and structures 206b). For structures having subresolution features (e.g., target of FIG. 4B), the edge of each set of subresolution lines (e.g., the first layer lines of set 452a) would be measured as a single edge.

Another COS determination technique is referred to as the correlation technique. In this technique, an initial COS position is estimated between the ROI's of the structures of each layer in operation 608. As shown for the structures 206, an initial estimate of COS 210 may be positioned between structures 206a and 206b. Two linear arrays are then obtained by measuring across the two sets of structures at positions that are equal distances from the initial COS. The structures 206a and 206b will tend to each result in a periodic signal with three peak intensity values. The two obtained linear arrays are then flipped horizontally and vertically and matched and a metric of correlation such as the product is calculated. The arrays are moved with respect to one another and the metric is calculated for each offset. The metric is then plotted and the correct COS is located by finding the maximum of the correlation metric. Intelligent searching algorithms (e.g., a binary search) may also be used to efficiently locate the correct COS position.

Said in another way, for each ROI set of each layer, its 180° rotation counterpart is automatically placed based on the initial COS in operation 610. The COS is continually moved for each layer until the best correlation is found between the rotated image and original images of each layer in operation 612. After the best correlation is found, the COS is found.

After the COS is found using any suitable technique, it is then determined whether the COS of the first layer structures differs from the COS of the second layer structures by more than a predetermined value in operation 614. If they do not differ by more than the predetermined value, it is determined that the x or y target under analysis in not out of specification in operation 618. However, if they do differ by more than the predetermined amount, it is determined that the x or y target under analysis is out of specification in operation 616. The procedure for determining whether the target is out of specification then ends.

The techniques of the present invention may be implemented in any suitable combination of software and/or hardware system. Regardless of the system's configuration, it may employ one or more memories or memory modules configured to store data, program instructions for the general-purpose inspection operations and/or the inventive techniques described herein. The program instructions may control the operation of an operating system and/or one or more applications, for example. The memory or memories may also be configured to store layout patterns, layout constraint rules and target rules.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A semiconductor target for determining a relative shift between two or more successive layers of a substrate, the target comprising:

a plurality of first structures formed in a first layer, and the first structures having a first center of symmetry (COS), the first structures being aperiodic; and a plurality of second structures formed in a second layer, and the second structures having a second COS, the second structures being aperiodic, wherein the difference between the first COS and the second COS corresponds to an overlay error between the first and second layer and wherein the first and second structures have a 180° rotational symmetry, without having a 90° rotational symmetry, with respect to the first and second COS, respectively.

2. The target of claim 1, wherein the first and second structures are in the form of device structures.

3. The target of claim 1, wherein the first structures include a first set of sub-structures that each has a first shape and a second set of sub-structures that each has a second shape that differs from the first shape.

4. The target of claim 3, wherein the second structures include a third set of sub-structures that each has a third shape and a fourth set of sub-structures that each has a fourth shape that differs from the third shape.

5. The target of claim 4, wherein the first, second, third, and fourth shapes differ from each other.

6. The target of claim 1, wherein the first and second structures are image-based overlay targets.

7. The target of claim 1, wherein a difference between the first COS and the second COS that is greater than a known offset between the first and second COS corresponds to an overlay error between the first and second layer.

8. The target of claim 1, further comprising an opaque layer deposited over the first or second structures.

9. The target of claim 1, wherein the first or second layer is a dummy layer.

10. A wafer having the target of claim 1 and a plurality of dies, wherein the target is formed in a scribe line located between at least some of the dies.

11. A wafer having the target of claim 1 and a plurality of dies, wherein the target is formed within a one of the dies.

* * * * *